United States Patent
Warren et al.

(10) Patent No.: US 7,404,707 B2
(45) Date of Patent: Jul. 29, 2008

(54) SAMPLE MOUNTING PRESS

(75) Inventors: Dwight F. Warren, Littleton, CO (US); Robert S. Tate, South Haven, MI (US); Matthew D. Cox, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 365 days.

(21) Appl. No.: 10/125,204

(22) Filed: Apr. 18, 2002

(65) Prior Publication Data

US 2003/0091676 A1 May 15, 2003

Related U.S. Application Data

(60) Provisional application No. 60/285,674, filed on Apr. 23, 2001.

(51) Int. Cl.
*B29C 43/32* (2006.01)

(52) U.S. Cl. .......... 425/78; 425/128; 425/193; 425/355; 425/DIG. 47

(58) Field of Classification Search ........ 425/128, 425/116, 188, 193, 78, 355, DIG. 47
See application file for complete search history.

(56) References Cited

U.S. PATENT DOCUMENTS

| | | | | | |
|---|---|---|---|---|---|
| 2,473,284 | A | * | 6/1949 | Knaggs | 425/546 |
| 3,599,578 | A | * | 8/1971 | Sato | 425/78 |
| 3,830,607 | A | * | 8/1974 | Baxendale et al. | 425/78 |
| 3,922,127 | A | * | 11/1975 | Schwarzkopf | 425/78 |
| 3,958,910 | A | * | 5/1976 | Wilde | 425/127 |
| 4,055,205 | A | * | 10/1977 | Withoff et al. | 425/DIG. 47 |
| 4,534,721 | A | * | 8/1985 | Iwasaki et al. | 425/73 |

* cited by examiner

*Primary Examiner*—Yogendra Gupta
*Assistant Examiner*—Thu Khanh T Nguyen
(74) *Attorney, Agent, or Firm*—Price, Heneveld, Cooper, DeWitt & Litton, LLP

(57) ABSTRACT

A hydraulic sample mounting press utilizes a face seal against the top face of a molding cylinder. The face seal employs a hydraulic cylinder to press a disk-shaped surface of a cap piece against the top annular face of the mold cylinder for a metallographic mounting press. The face seal cylinder is mounted to a hydraulic fluid column that allows the face seal to rotate away from the mold cylinder for access to the molding cylinder and to rotate into place when a metallographic mount is to be molded.

8 Claims, 6 Drawing Sheets

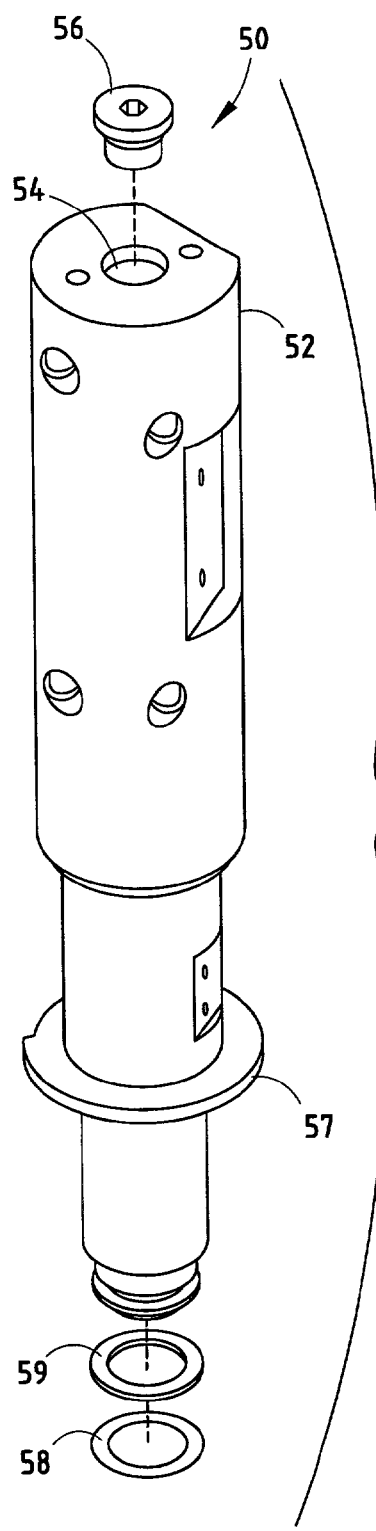
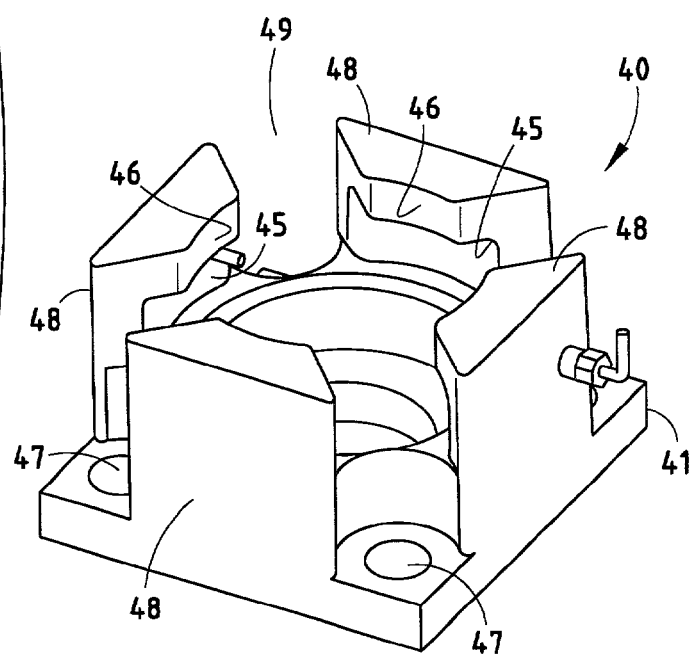
FIG. 7
FIG. 9

SAMPLE MOUNTING PRESS

CROSS-REFERENCE TO RELATED APPLICATIONS

This application claims priority under 35 U.S.C. § 119(e) on U.S. Provisional Application No. 60/285,674 entitled SAMPLE MOUNTING PRESS, filed on Apr. 23, 2001, by Cox et al., the entire disclosure of which is incorporated herein by reference.

BACKGROUND OF THE INVENTION

The present invention relates to a mounting press for metallographic samples and particularly to an improved seal structure for the molding chamber.

Mounting presses are employed to mold a thermoplastic or thermosetting material around typically a metallic specimen for ease of handling in subsequent polishing and analyzing processes. Such mounting presses include a cylindrical mold chamber into which an upper closure ram and a lower hydraulically driven ram extend, such that the molding material and sample are held and compressed between the rams.

The standard upper closure ram uses a handle to move a radially sealing upper ram into the bore of the molding cylinder at the top. This mechanism is then locked into place with a quarter turn, bayonet-type device or by using coarse threads. This style of enclosure requires considerable manipulation by the operator especially if they have to turn the mechanism to engage threads. Opening of this type of closure is also difficult since, during the molding process, pressure builds up between the lower ram and the removable, upper closure ram of the mold cylinder. This pressure on the quarter turn device or the threads makes it very difficult for the user to spin the mechanism open. Regularly a length of pipe or some other type of lever must be used to gain a mechanical advantage to open the mold cylinder. Also, blowby flashing tends to make the upper closure ram stick within the mold cylinder. Once open, any residual material or "flashing" left on the upper ram of the closure device must be cleaned prior to sliding the upper ram back into the bore of the mold cylinder.

SUMMARY OF THE INVENTION

The invention is a departure from such traditional mounting press enclosure systems. The hydraulic enclosure system of this invention avoids the cumbersome radial seal altogether and instead utilizes a face seal which engages the top face of the mold cylinder. This face seal is actuated by a hydraulic cylinder which presses a sealing cap piece against a top annular sealing face of the mold cylinder. When this cap piece has formed a face seal, the metallographic mount is molded. When the face seal is removed, the internal pressure of the mold is immediately released and an upper enclosure containing the cap piece is readily moved away from the mold cylinder to expose a mount and specimen contained therein for fast, easy removal. In a preferred embodiment, the hydraulic cylinder and cap piece is mounted to a cylindrical column that allows it to rotate away from the mold cylinder when the mount is complete and rotate into place when a mount is to be made. The column that acts as the rotational device also delivers the hydraulic fluid to the upper hydraulic cylinder so there is no need for a hose or other hydraulic connection. Also, the cap piece and top face of the mold cylinder do not need to be cleaned between mounts. This enclosure system also allows the workable height of the system to be lower and makes it more accommodating for the operator since it minimizes user interaction with the mold process and prevents user exposure to hot mechanism. Further, the hydraulic system in one embodiment combines the hydraulic cylinders, manifold, valving, pump, reservoir, transducers, rotary seal, and accumulator into one assembly eliminating hydraulic hoses and fittings between components, which virtually eliminates hydraulic leak potential.

These and other features, objects and advantages of the present invention will become apparent upon reading the following description thereof together with reference to the accompanying drawings.

BRIEF DESCRIPTION OF THE DRAWINGS

FIG. 7 is an exploded perspective view of the pivoted hydraulic supply cylinder seen also in FIG. 3;

FIG. 9 is a perspective view of the mold adapter block shown in FIGS. 3 and 8.

DETAILED DESCRIPTION OF THE PREFERRED EMBODIMENT

Figure 1:
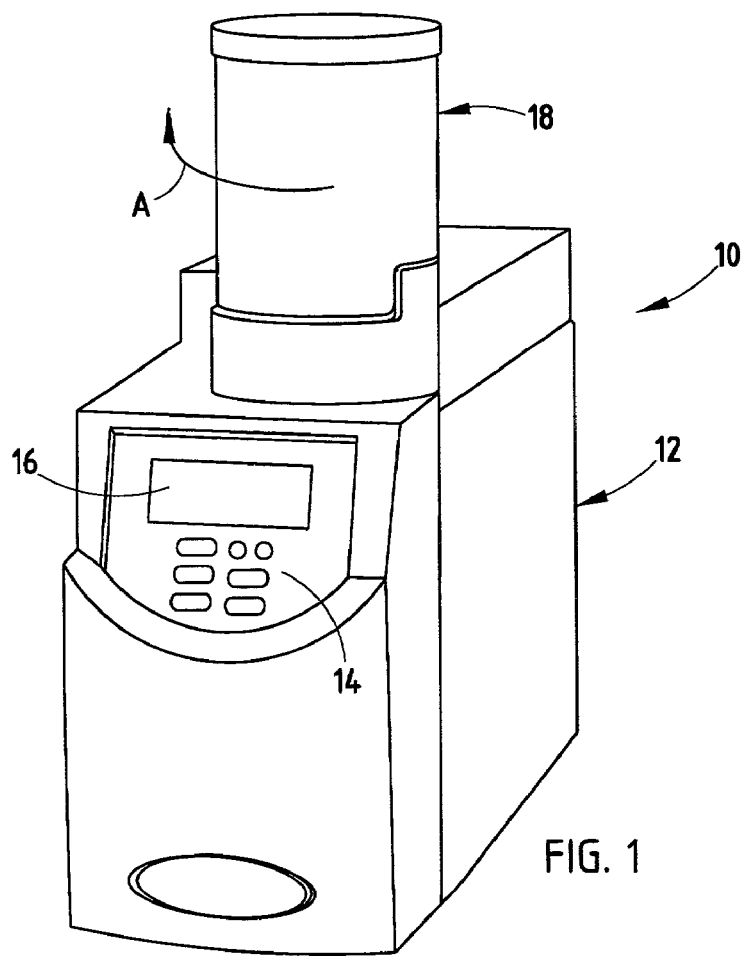
FIG. 1 is a perspective view of a sample mounting press embodying the present invention.

Referring initially to FIG. 1, there is shown a sample mounting press 10 embodying the present invention which comprises a lower cabinet 12 housing a keypad 14 and display 16 for the operation of the unit. Mounted within cabinet 12 is the mold cylinder assembly 30 (FIGS. 3, 5 and 8) and a lower ram assembly including a mold adapter block 40, a hydraulic cylinder 84, and a manifold 42 coupled to a hydraulic pump 41 providing a hydraulic fluid system pressure of approximately 3000 pounds for operation of the various hydraulic cylinders employed in the system.

Figure 2:
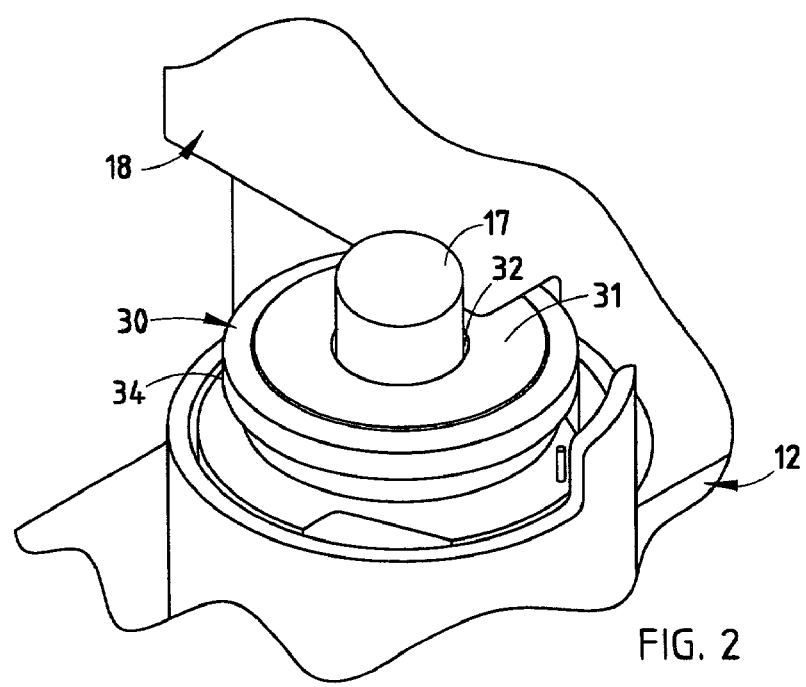
FIG. 2 is a fragmentary right-side perspective view of the upper pivoted section of the assembly shown in FIG. 1, shown with the upper face sealing cylinder pivoted to a position exposing the mold cylinder assembly and showing a metallographic molded sample in position for removal therefrom.
Figure 4:
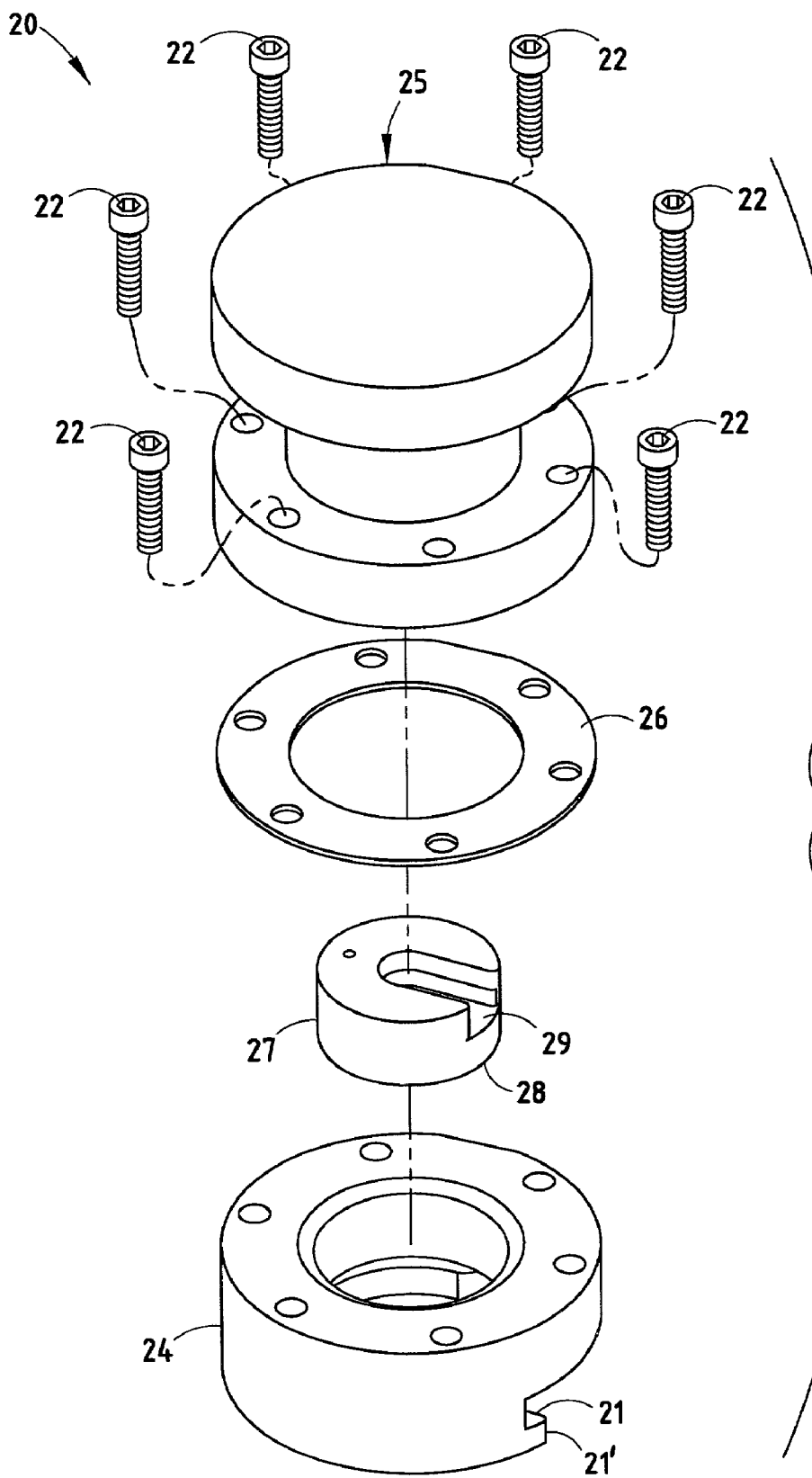
FIG. 4 is an exploded perspective view of the face seal assembly.
Figure 5:
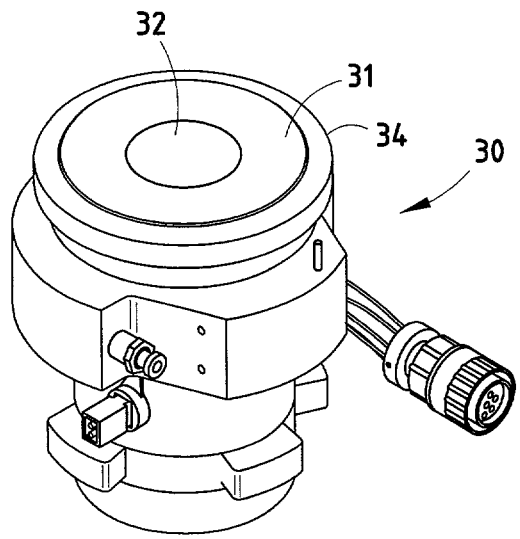
FIG. 5 is a perspective view of the mold cavity subassembly.
Figure 6:
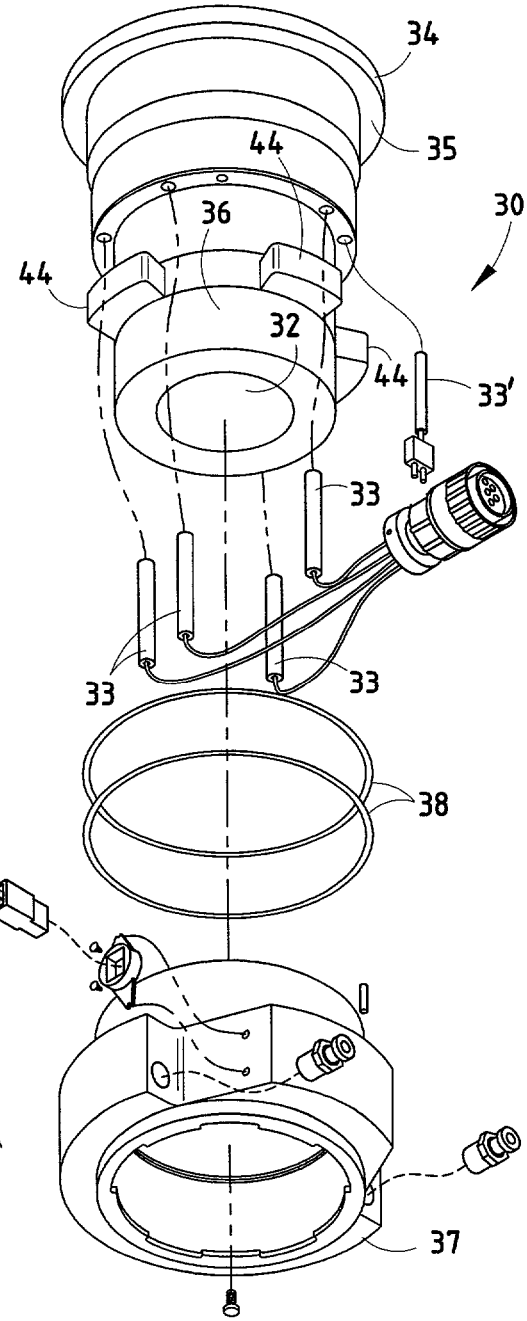
FIG. 6 is an exploded lower perspective view of the structure shown in FIG. 5.

Pivotally mounted with respect to cabinet 12 is an upper face seal assembly 20 (FIGS. 3, 4, and 8) which, as seen in FIGS. 1 and 2, is mounted in an upper enclosure 18 which can pivot to the left (shown by arrow A in FIG. 1) to expose the top sealing face plate 31 of the mold cylinder assembly 30, shown in detail in FIGS. 5 and 6. This exposes the cylindrical mold cavity 32 to allow the operator to remove the metallographic sample encapsulated in a molding material as a unit in disk-shaped sample mount 17 (FIG. 2) as described below.

Figure 3:
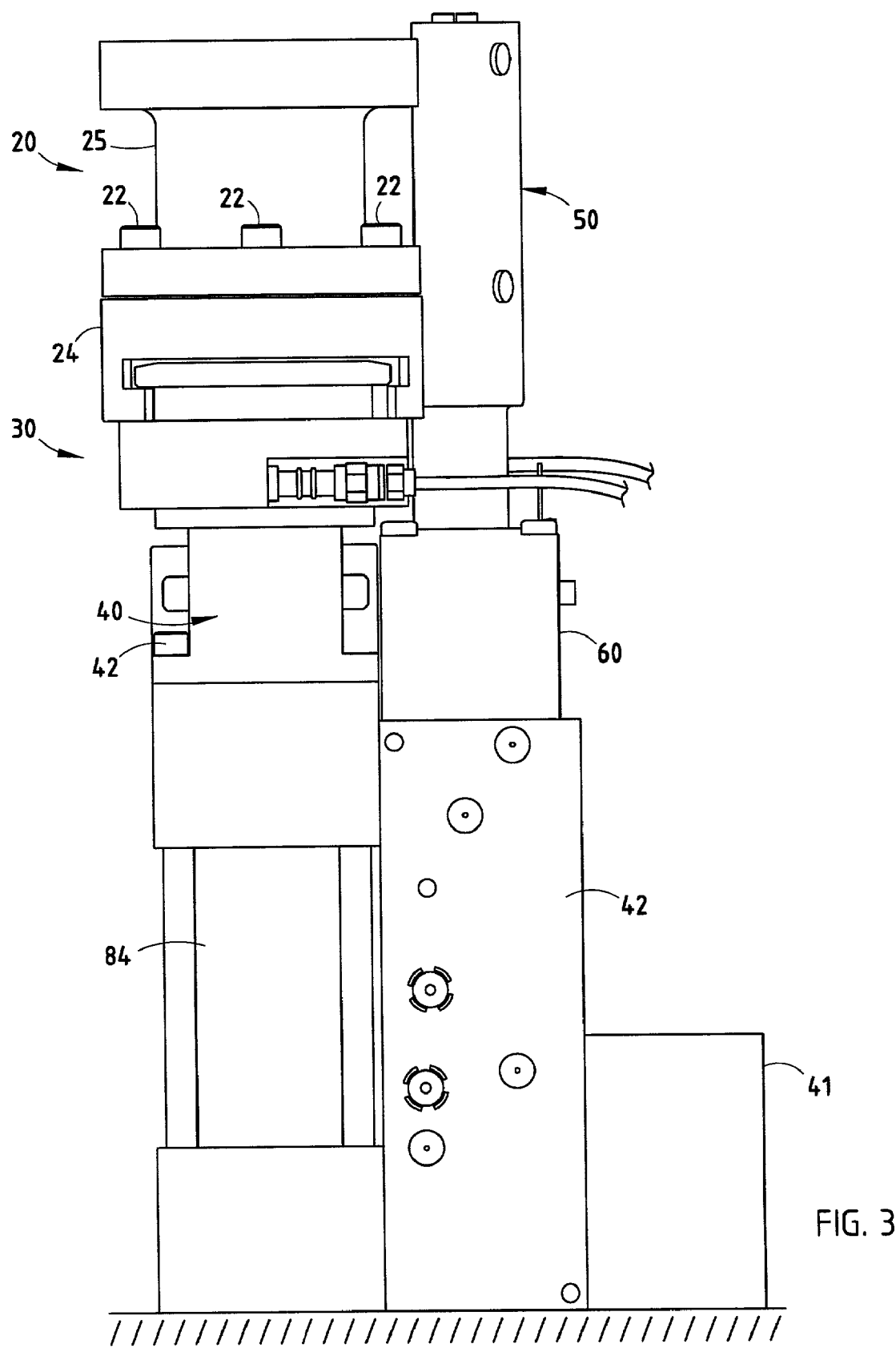
FIG. 3 is a side elevational view of the sample mounting press.

The upper face seal assembly 20 is shown in FIG. 4 and includes a pancake hydraulic cylinder 25 which is coupled by a thermal gasket 26 and fasteners 22 to a cylindrical flange 24 with the completed assembly shown in FIG. 3. Cylinder 25 includes a movable piston rod 23 (FIG. 8) having an enlarged end over which the sealing cap piece 27 extends via an under-cut slot 29 (FIG. 4). Metal cap 27 is rigid and defines a rigid face seal 28 which sealably engages the top annular sealing surface 31 of mold cylinder assembly 30, as best seen in FIG.

Figure 8:
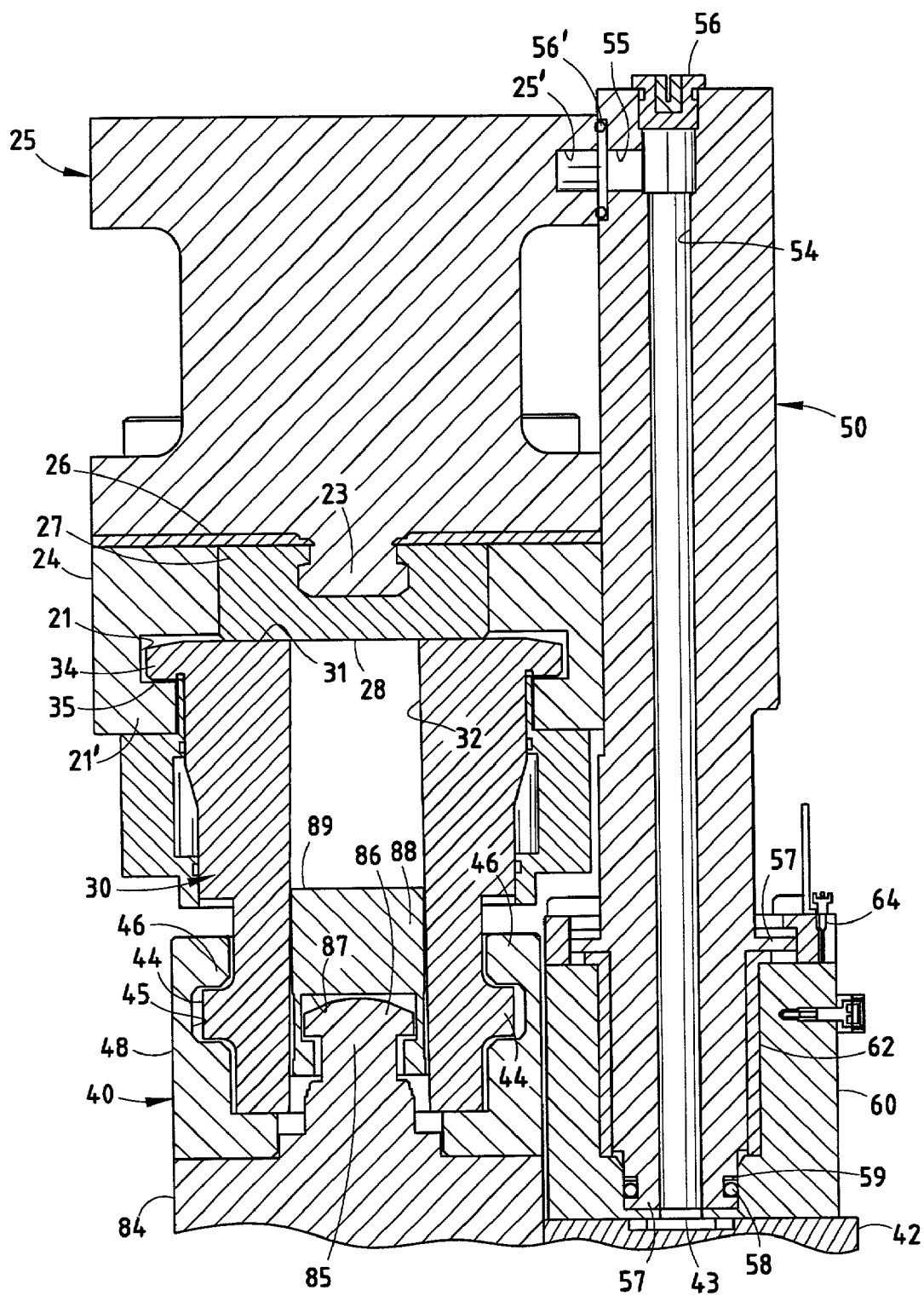
FIG. 8 is a fragmentary vertical cross-sectional view of the sample mounting press.

8. Flange 24 also includes an undercut slot 21 (FIG. 4) which defines a shoulder 21' that lockably engages circular flange 34 of mold assembly 30 (as also best seen in FIG. 8) to lock the face seal assembly 20 to the mold assembly 30 during the molding process. Thus, semi-annular shoulder 21' (FIG. 4) circumscribes an arc which is open sufficiently such that cylindrical flange 34 can be received within slot 21. When closed as seen in FIG. 8, the upper surface of shoulder 21' engages the lower surface 35 of the flange 34 of the mold assembly 30 to lock the face seal assembly to the upper end of the mold cavity, thereby allowing the sealing pressure to be applied to effect the face seal by cylinder 25.

The pancake hydraulic cylinder 25 is sealably coupled to a cylindrical column or pressure rotary coupling 50 (FIGS. 7 and 8), which receives pressurized hydraulic fluid from pump 41 via manifold 42. The pressure rotary coupling 50 has a generally cylindrical body 52 with a central bore 54 therein capped by sealing cap 56 at its upper end. A radially extending opening 55 is sealably coupled to the input 25' of pancake cylinder 25 by means of an O-ring sealing gasket 56', as best seen in FIG. 8. The lower end of pressure rotary coupling 50 is rotatably mounted within a mounting plate 60 by means of a sleeve bearing 62. Hydraulic pressure is applied to the cylindrical bore of rotary coupling 50 at its lower end from manifold 42 via port 43 (FIG. 8). Suitable valves are provided to selectively apply pressure during the sealing and molding process in a conventional manner. The lower end 57 of rotary coupling 50 is sealably mounted within the bushing 52 and block 60 by means of an O-ring seal 58 and back up ring seal 59 (FIGS. 7 and 8), which allows rotation of the upper seal assembly 20 coupled to rotary coupling 50 between a closed position, as shown in FIGS. 1 and 8, and an open position, shown in FIG. 2, by the rotation of rotary coupling 50 with respect to the fixed mounting block 60. Rotary coupling 50 is held in block 60 by an annular flange 57 integral with the body 52 of the rotary coupling and an annular clamp 64 (FIG. 8) secured to block 60, in turn, suitably secured within cabinet 12.

Mold cylinder assembly 30 (FIGS. 5 and 6) includes four cartridge heaters 33 (FIG. 6) positioned in radially spaced relationship around the peripheral of the cylindrical body 36 of the mold assembly 30, which is conventionally surrounded by a cylindrical water jacket 37 sealed by pairs of spaced O-rings 38. A thermocouple 33' is also inserted into the body 36 of mold cylinder assembly 30 and is employed in connection with a control circuit to provide the desired molding temperature within the cylindrical mold cavity 32 by heaters 33 during the molding process. The mold cylinder assembly 30 includes four radially outwardly extending arcuate flanges 44 spaced at approximately 90° intervals and circumscribing an arc of about 30° to 40° to interlock with the lower mounting block 40, as seen in FIG. 8. Block 40, as best seen in FIG. 9, includes a base plate 41 which is bolted by bolts 42 (FIG. 3) extending into through apertures 47 into the top of hydraulic cylinder 84. Cylinder 84 includes a piston 85, as seen in FIG. 8, extending upwardly and which is captively held with its enlarged head 86 fitted within an undercut open slot 87 in a lower ram 88 enclosing the lower end of cylindrical mold chamber 32. The mounting block 40 includes four upwardly extending shoulders 48, each of which include an undercut 45 which defines shoulders 46. The arcuate shoulders 46 are spaced at 90° intervals with slots 49 extending between adjacent shoulders 46 to allow the insertion of flanges 44 therein to bayonet-lock mold assembly 30 to block 40. Shoulders 46 engage and lock flanges 44 of mold assembly 30 into locked engagement with cylinder 84, such that pressure can be applied to the lower end of the cylindrical mold chamber 32 by ram 88 when actuated by hydraulic pressure from manifold 42 coupled to cylinder 84 by a suitable valve. Hydraulic cylinder 84 is actuated at approximately 3000 psi system pressure during an operating cycle to extend ram 88 upwardly into the chamber 32 of cylindrical mold assembly 30 while the top surface 31 of the mold chamber is sealed by the face seal 28 to compress the polymeric thermosetting material around and onto a metallographic specimen.

During a cycle of operation, the upper assembly 18 is opened to the position shown in FIG. 2, and ram 88 is raised by the actuation of cylinder 84 to present the top disk-shaped surface 89 of ram 88 to an operator for placing a metallographic sample thereon. Subsequently, cylinder rod 85 and ram 88 are retracted slightly into the cylindrical mold cavity 32 of mold body 36. Resin is then placed into the mold cavity 32, and the upper assembly 18 pivoted using rotary coupling 50 to a closed locked position. The pancake hydraulic cylinder 25 is then actuated to form the face seal at the upper end of the mold chamber 32. Heat and pressure is then applied to the molding material by heaters 33 and compression through lower cylinder 84 to the thermosetting material for a predetermined period of time sufficient to mold the material around the metallographic sample. A conventional thermosetting or thermoplastic resin into which the metallographic sample is encapsulated is melted under an internal mold pressure of from about 2000 psi to about 4200 psi at about 300° F. The molding process takes from 6 to 20 minutes depending upon the material employed, which may include polycarbonate, phenolics, epoxies, or other resins typically employed for molding metallographic samples for use in metallographic analysis equipment. After the heating and pressure steps, mold assembly 30 is cooled either using water applied to the water jacket 37 for cooling the chamber or, in the case of thermoplastic resin, it is air cooled. The pressure on cylinders 25 and 84 is then released by suitable valving to allow the upper unit 18 to again pivot to an open position. The metallographic sample disk-shaped mount 17 is removed from the device by again applying some hydraulic pressure to cylinder 84 to eject the mount 17, as seen in FIG. 2. By providing a face seal which is readily moved away from the mold chamber and by activating cylinder 84, the disk-shaped mount is pushed out of the cylindrical mold chamber 32, and the prior art difficulties with opening the upper end of the mold cavity is eliminated through the use of the face seal 28. The body of the mold cavity and the cap piece forming the face seal can be made of metals typically used for sample mounting presses, such as stainless steel, aluminum alloys, or the like. The sealing surfaces 28 and 31 of the respective members are polished to form a leak-free seal when cylinder 25 is actuated by a pressure of about 3000 psi.

It will become apparent to those skilled in the art that various modifications to the preferred embodiment of the invention as described herein can be made without departing from the spirit or scope of the invention as defined by the appended claims.

The invention claimed is:

1. A metallographic sample mounting press comprising:
   a sample molding chamber open at opposite ends;
   a ram extendable into said sample molding chamber from one end for compressing a sample molding material therein;
   a face seal assembly removably secured to an end of said chamber opposite said ram, said assembly having a face seal for sealing said opposite end of said molding chamber;
   a cylinder is coupled to said face seal for selectively causing said face seal to seal said opposite end of said sample molding chamber for molding a sample holding material around a metallographic sample, wherein said opposite end of said sample molding chamber includes a generally disk-shaped face plate which is engaged by said face seal;

wherein said face seal assembly includes a cylindrical flange having a shoulder with an annular slot formed therein and said face plate is formed on a flange which extends in said annular slot to lockably hold said face seal assembly to said molding chamber;

wherein said face seal includes a disk-shaped cap piece having a polished surface which sealably engages said face plate to seal the opposite end of said mold chamber; and wherein said face seal assembly is movably mounted with respect to said mold chamber and is pivoted from a first position axially aligned with said mold chamber for sealing said mold chamber and a second position displaced from said first position for gaining access to said mold chamber.

2. The press as defined in claim 1 wherein said face seal assembly includes a second hydraulic cylinder for rotatably moving said face seal assembly into and out of alignment with said molding chamber.

3. A metallographic sample mounting press comprising:
a cylindrical sample molding chamber open at opposite ends;
a ram extendable into said sample molding chamber from one end for compressing a sample molding material around a metallographic sample;
a rigid face seal assembly movably positioned with respect to said sample molding chamber at a second end opposite said ram for movement between a first position aligned with said molding chamber and a second position angularly displaced from said molding chamber, said face seal assembly including a disk-shaped sealing member having a flat surface with a diameter greater than the diameter of said cylindrical sample molding chamber to form the only seal of said sample molding chamber at said second end; and
a cylinder coupled to said sealing member for rotating said sealing member to form an external face seal at said second end of said sample molding chamber for enclosing said sample molding chamber during the molding of a sample holding material around a metallographic sample.

4. The press as defined in claim 3 wherein said opposite end of said sample molding chamber includes an annular face plate.

5. The press as defined in claim 4 wherein said face seal assembly further includes a cylindrical flange having a shoulder with an annular slot formed therein for engaging the underside of said face plate to selectively lockably engage said face seal assembly to said molding chamber.

6. The press as defined in claim 5 wherein said sealing member includes a disk-shaped polished surface which sealably engages said face plate to seal the opposite end of said mold chamber.

7. A metallographic sample mounting press comprising:
a sample molding chamber open at opposite ends;
a ram extendable into said sample molding chamber from one end for compressing a sample molding material therein;
a face seal assembly movably positioned with respect to said sample molding chamber at an end opposite said ram for movement between a first position aligned with said molding chamber and a second position angularly displaced from said molding chamber, said face seal assembly including a disk-shaped sealing member;
a cylinder coupled to said sealing member for selectively causing said sealing member to form a face seal at the opposite end of said sample molding chamber for molding a sample holding material around a metallographic sample;
wherein said opposite end of said sample molding chamber includes an annular face plate;
wherein said face seal assembly further includes a cylindrical flange having a shoulder with an annular slot formed therein for engaging the underside of said face plate to selectively lockably engage said face seal assembly to said molding chamber;
wherein said sealing member includes a disk-shaped polished surface which sealably engages said face plate to seal the opposite end of said mold chamber; and
wherein said face seal assembly includes a rotary coupling for rotatably moving said face seal assembly into and out of alignment with said molding chamber.

8. A metallographic sample mounting press comprising:
a cylindrical molding chamber open at opposite ends;
a ram extendable into said sample molding chamber from one end for compressing a sample molding material therein;
a face seal movably mounted at an opposite end of said chamber to selectively engage an outer surface of said opposite end of said chamber; and
a first activating element coupled to said seal for selectively causing said face seal to move in an axial direction to seal the opposite end of said sample mold chamber for molding a sample holding material around a metallographic sample, and further including a second activating element coupled to said face seal for moving said face seal in a radial direction with respect to said molding chamber.

* * * * *